United States Patent [19]

Farmer et al.

[11] Patent Number: 5,499,066
[45] Date of Patent: Mar. 12, 1996

[54] AN OPTICAL INSTRUMENT WITH A CONTINUOUSLY ADJUSTABLE ZOOM

[75] Inventors: John W. Farmer, Drouin; George Smith, Mt. Waverley; Malcolm Gin, Wonthaggi; John F. H. Brook, College Park; Daryl R. White; Brian A. See, both of Technology Park, all of Australia; Ian Powell, Gloucester, Canada

[73] Assignee: Remraf Pty. Ltd., Australia

[21] Appl. No.: 975,929

[22] PCT Filed: Aug. 26, 1991

[86] PCT No.: PCT/AU91/00387

§ 371 Date: Apr. 21, 1993

§ 102(e) Date: Apr. 21, 1993

[87] PCT Pub. No.: WO92/03085

PCT Pub. Date: Mar. 5, 1992

[30] Foreign Application Priority Data

Aug. 24, 1990 [AU] Australia .............. PK1934/90

[51] Int. Cl.$^6$ .............. A61B 3/12; G02B 15/00
[52] U.S. Cl. .......... 351/221; 351/205; 351/246; 359/362
[58] Field of Search ................. 351/205, 206, 351/211, 221, 216, 246; 359/362, 432

[56] References Cited

U.S. PATENT DOCUMENTS

| | | | |
|---|---|---|---|
| 4,248,505 | 2/1981 | Muchel et al. | 351/221 |
| 4,502,766 | 3/1985 | Ito | 351/206 |
| 4,666,262 | 5/1987 | Zobel | 359/380 |
| 4,666,268 | 5/1987 | Ito | 351/206 |
| 4,699,480 | 10/1987 | Pomerantzeff | 351/205 |
| 4,710,002 | 12/1987 | Pomerantzeff | 351/205 |
| 4,779,969 | 10/1988 | Sato et al. | 359/422 |

OTHER PUBLICATIONS

Pomerantzeff, et al., "An Optimized Zoom Ophthalmoscope", Opthalmology, vol. 91, No. 2, pp. 197–203, Feb. 1984.

*Primary Examiner*—William L. Sikes
*Assistant Examiner*—David R. Parsons
*Attorney, Agent, or Firm*—Knobbe, Martens, Olson & Bear

[57] ABSTRACT

An optical instrument for indirectly observing an object includes a first lens system for producing a first image of the object, and an adjustable second lens system for producing a second image of the object. The second lens system is continuously adjustable between a first position wherein the second image has maximum magnification and/or a minimum area of view, and a second position wherein the second image is of a minimum magnification and/or a maximum area of view. In one aspect of the invention, the second lens system is a zoom lens system having two substantially fixed conjugate planes. In another aspect of the invention, the instrument defines a folded optical path through the lens systems which includes a generally U-shaped portion so as, in use, to reduce the separation of the observer and the observed object.

21 Claims, 7 Drawing Sheets

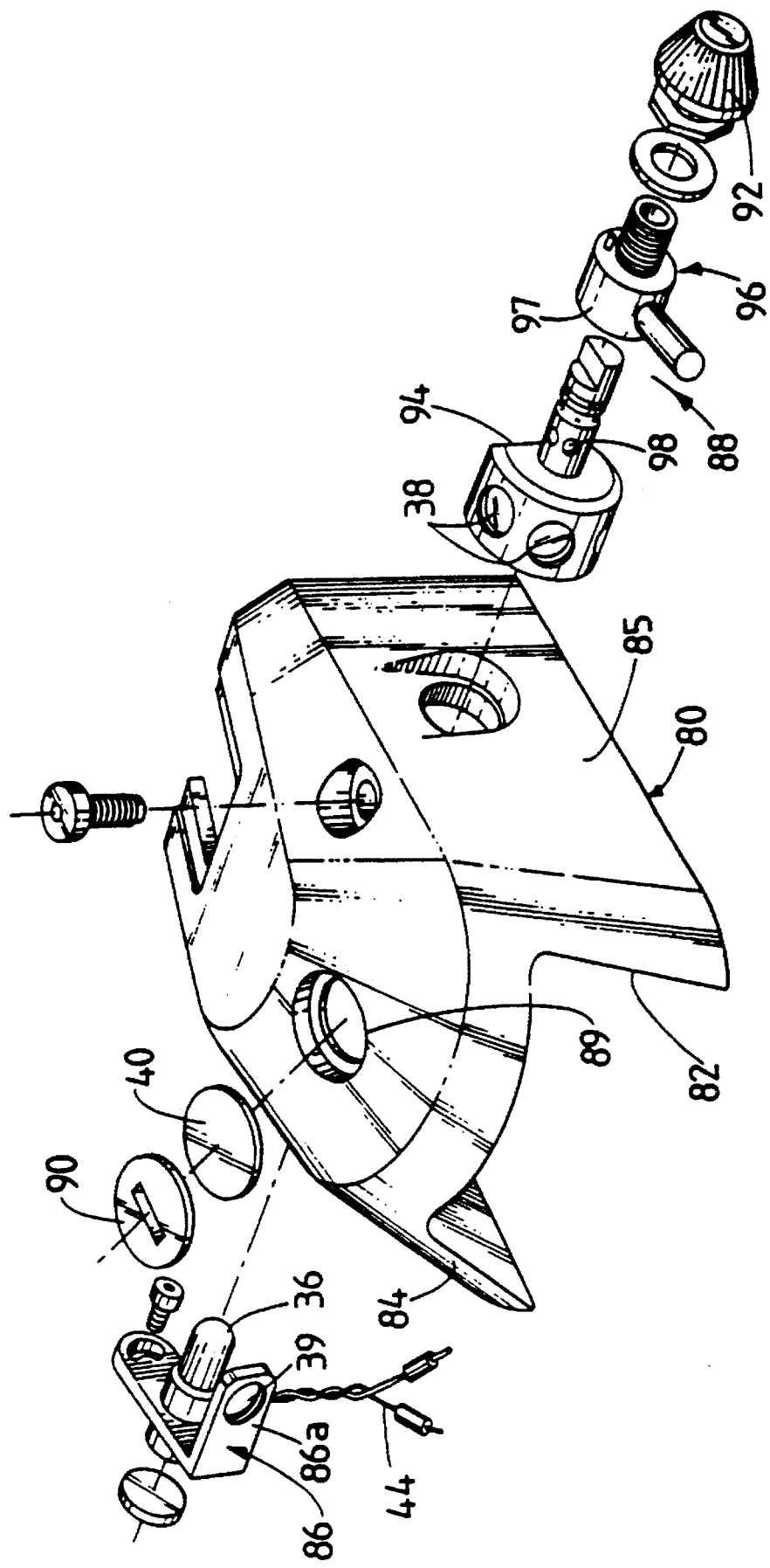

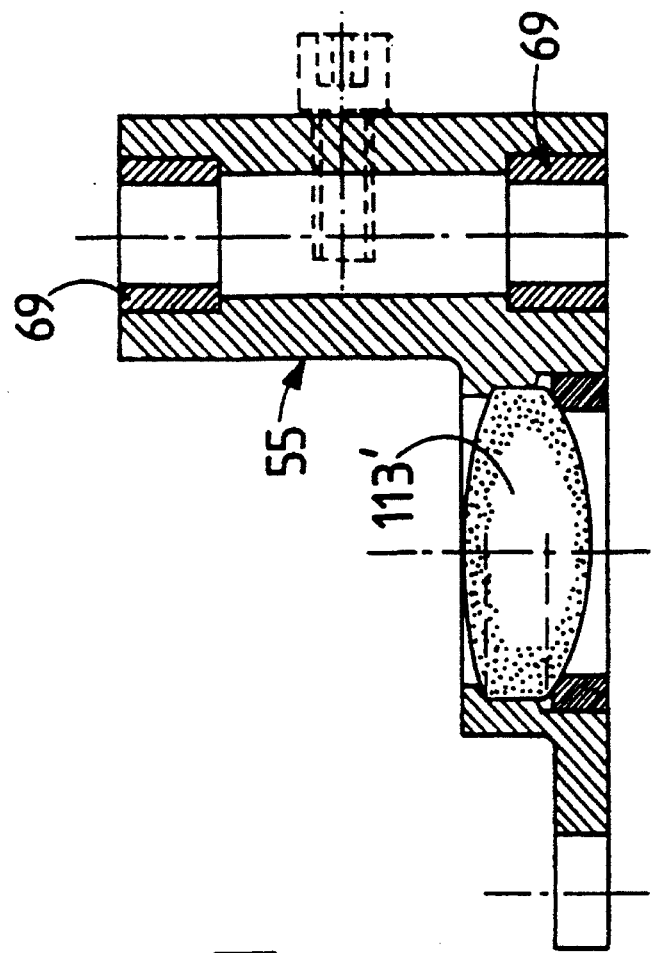
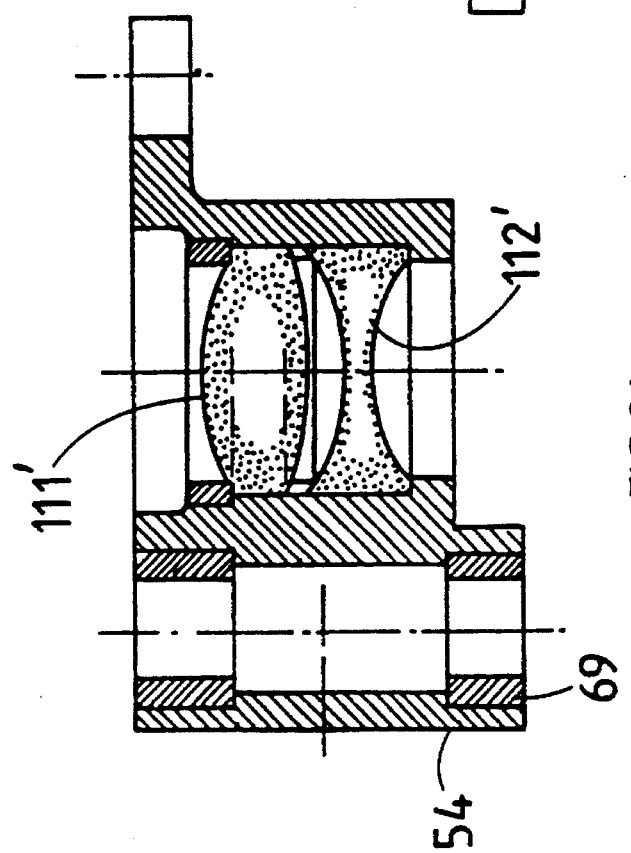

AN OPTICAL INSTRUMENT WITH A CONTINUOUSLY ADJUSTABLE ZOOM

FIELD OF THE INVENTION

The present invention relates generally to an optical instrument which has particular but by no means exclusive application as an ophthalmic instrument, eg in ophthalmoscopy.

Although the present invention will be described with particular reference to its application to ophthalmoscopes, it is to be noted that the present invention is not so limited and is more extensive m scope, extending in its application to other areas of optometry, ophthalmoseopy in ophthalmic surgery, and to diagnosis and treatment in other areas of medicine e.g. gynaecology and dentistry.

BACKGROUND ART

At present there are two basic types of ophthalmoscopes; the direct ophthalmoscope and the indirect ophthalmoscope. Both types have advantages in certain circumstances and disadvantages in other circumstances.

In the direct ophthalmoscope a light source is used to directly illuminate a patient's eye and the optical system of the patient's eye functions as a simple magnifier, thereby allowing the observer to see an erect, magnified image of the patient's fundus. The direct ophthalmoscope provides a means of illuminating the fundus and of observing the illuminated area. The illumination is usually provided by means of a light source and a reflecting prism or mirror whereby the beam of light can be conveniently directed through the pupil. It will be appreciated that the illuminated fundus is viewed under conditions analogous to a magnifying glass. The retina is at the focus of the dioptric system of the eye and consequently an erect, magnified, clearly focussed image of the fundus is observed. The magnification is about fifteen times depending on the condition and characteristics of the observer's and patient's eyes, but the field of view is quite small, only about 6½or thereabouts. The actual area of the fundus in view at any time also depends upon the distance of the observer from the pupil of the patient's eye, and to a small extent on the patient's pupil diameter. Thus, while the direct ophthalmoscope provides an erect and relatively highly magnified image, the actual area of the eye being viewed is quite small and an extensive scan of the entire surface of the eye is required in order to gain a complete picture of the eye at this magnification.

In the indirect ophthalmoscope, which can be either binocular or monocular, a condensing lens positioned in front of the patient's eye produces an inverted image of the patient's retina. This image can then be viewed by the observer either with or without the aid of additional lens systems. With most commercial instruments, the condensing lens is hand-held and the lens system is mounted on a head band, although a hand-held device and a spectacle configuration are available. In most cases, the observed image is inverted, Ln some it is not, The retinal image is viewed with a magnification in the range 2.5 to 5 times and a field of view generally around 35° to 65°, depending on the precise optical configuration. Thus, the indirect ophthalmoscope, when provided with a suitable relay lens system, provides an inverted or erect image which is only moderately magnified but entails a relatively extensive field of view compared with direct ophthalmoscopes.

From the foregoing it is clear that there is a compromise in the use of both types of ophthalmoscopes. Whereas the direct instrument produces a greatly magnified image, it has a very small field of view and the indirect instrument has a large field of view but produces an image which is only slightly magnified. Accordingly, both instruments must be used in conjunction with each other for a full comprehensive study of a patient's eye when attempting to detect an abnormal condition. One problem with using two instruments is that when an area of interest with respect to an abnormal condition is located, say using the indirect ophthalmoscope because of its large field of view, the magnification is not great enough to investigate fully the precise nature of the abnormality. However, when an observer changes to the direct ophthalmoscope in order to view the abnormality under increased magnification, the precise location of the abnormality cannot be easily determined and a scan of the eye must be undertaken to locate the exact position of the abnormality. Therefore, an operator is continually confronted by a compromise situation as to which type of instrument to use and many investigations require the successive or alternate use of the two different instruments.

U.S. Pat. Nos. 4502766 and 4666268 disclose fundus cameras incorporating a zoom lens system for varying magnification and field of view. This concept is, however, not readily applicable to ophthalmoscopes With the arrangement disclosed in these patents, the observer will need to adjust the position of his eye as the zoom lens system is adjusted. This is not a serious objection for an instrument having the primary function of recording a photographic image, but would render an ophthalmoscope less than satisfactory. A linear optical configuration of the kind proposed for the fundus cameras of the aforementioned US patents would also render an ophthalmoscope somewhat cumbersome in use.

SUMMARY OF THE INVENTION

It is an object of the present invention to provide an instrument which at least alleviates one or more of the problems of using two instruments by providing a single instrument which has at least in part the advantages of both types.

According to a first aspect of the present invention there is provided an optical instrument for indirectly observing an object, comprising a first lens system for producing a first image of the object, and an adjustable second lens system for producing a second image of the object. The second lens system is continuously adjustable between a first position wherein the second image has maximum magnification and/or a minimum area of view and a second position wherein the second image is of a minimum magnification or/and a maximum area of view. The second lens system is a two-conjugate zoom lens system, preferably an a focal system having one pair of substantially infinite conjugate planes.

In a second aspect of the invention, there is provided an optical instrument for indirectly observing an object, comprising a first lens system for producing a first image of the object, and an adjustable second lens system for producing a second image of the object. The second lens system is continuously adjustable between a first position wherein the second image has maximum magnification and/or a minimum area of view and a second position wherein the second image is of a minimum magnification or/and a maximum area of view. The optical instrument defines a folded optical path through said lens systems which includes a generally U-shaped portion so as, in use, to reduce the separation of the observer and the observed object.

A particularly preferred embodiment of the invention incorporates both of the above aspects.

BRIEF DESCRIPTION OF THE DRAWINGS

The present invention will now be described, by way of example only, with reference to the accompanying drawings, in which:

FIG. 7 is an exploded view of the cover and its retained components;

FIGS. 8A and 8B show the moveable zoom lens components in cross-section.

DESCRIPTION OF PREFERRED EMBODIMENT(S)

Figure 1:
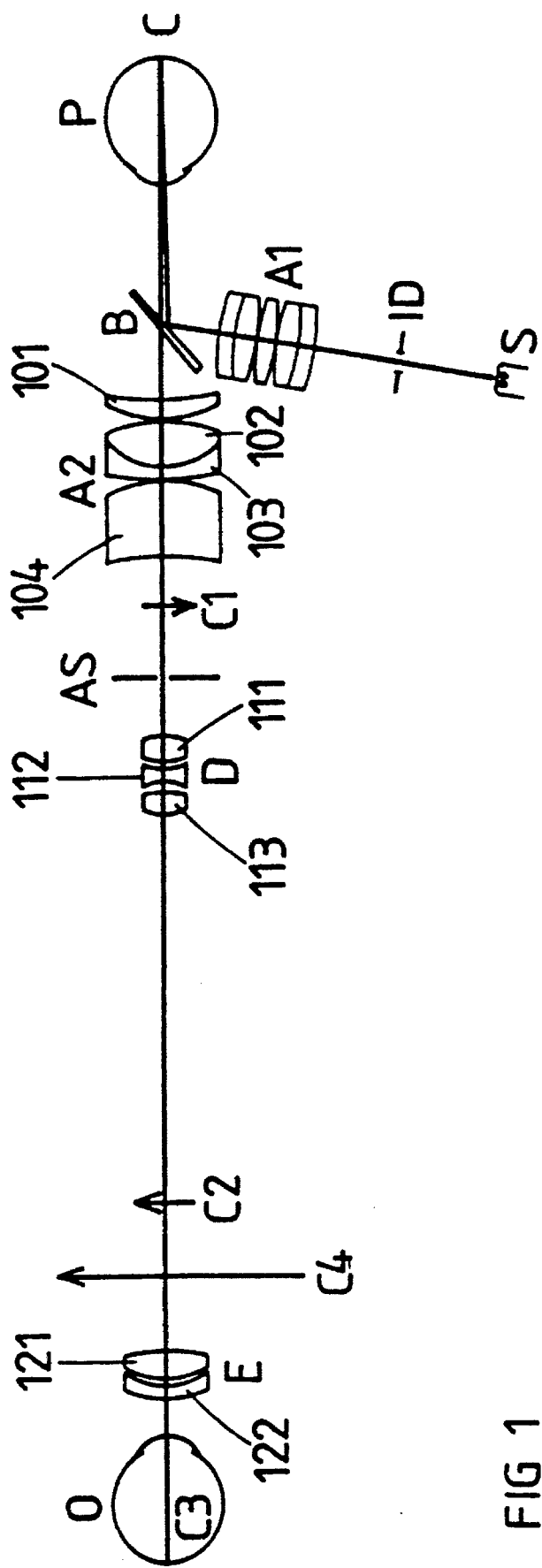
FIG. 1 is an optical diagram of a straight-line form of ophthalmoscope incorporating an embodiment of the first aspect of the present invention.

In FIG. 1, the patient's eye, represented by P, is shown at the right hand side of the drawing while the observer's eye, represented by O, is shown at the left hand side. A light source, for example the glowing filament of an incandescent bulb or similar, represented by S, is located in the handle portion of the ophthalmoscope. Light emitted from the light source and represented by the ray line 2 travels in the direction of arrow 3 through an iris diaphragm, ID, to a beam splitter B. The opening of iris diaphragm ID is adjustable to vary the intensity of light passing to the patient's eye and also to vary the field of view of the patient's eye. A first lens system A1 of fixed overall focal length comprising a number of different lens elements is located between the iris diaphragm ID and beam splitter B to focus the light from source S. One form of beam splitter B is a mirror for directing reflected light 4 towards the patient's eye P. However, other forms of beam splitter B are contemplated such as, for example, a prism or the like. Light falling on the retina C of the patient's eye P brightly illuminates the area of the retina it is wished to observe. The area of the retina illuminated can be controlled by means of the setting of iris diaphragm, ID, and by scanning the patient's eye.

Light 6 reflected from the retina C passes through the patient's eye including the lens and cornea of the eye to beam splitter B. After passing through beam splitter B the light 7 travels to a lens system A2 of fixed overall focal length which focuses the light 7 at C1. Additionally, the second lens system A2 images the patients pupil at aperture stop AS. Thus, the image C2 of the fundus of the patient's eye at C1 is inverted.

Zoom lens system D is located intermediate the second lens system A2 and eye piece lens system E. Zoom lens system D forms an erect image C2, ie the inverted image of C at C1 is again inverted to form an erect image at C2. In addition to erecting the image, lens D may also magnify the image. Eyepiece lens system E magnifies the image C2 so as to form an erect magnified image C3 on the observer's retina. The eyepiece containing lens system E is adjustable to an extent to provide a proper focus for the observer.

Zoom lens system D comprises a plurality of lens elements which are arranged with respect to one another so as to be continuously variable between a first position in which the magnification is at a minimum, such as for example when the image is formed at C2 of FIG. 1, and a second position in which the magnification is at a maximum, such as for example when the image is formed at C4 of FIG. 1. In accordance with the first aspect of the invention, lens system D is a two-conjugate lens system so that the image positions of both the patient's retina and the patient's pupil do not move during zooming, ie they remain in the same pair of fixed planes during zooming. Thus, although not depicted in FIG. 1, the positions of $C_2$ and $C_4$ coincide, i.e. are coincident so as to comprise a fixed pair of conjugate planes. Furthermore, it is preferred that zoom lens system D is an afocal system having one pair of substantially infinite conjugate planes.

In one form, zoom lens system D is continuously adjustable between its limiting positions in order to provide images of any magnification and/or fields of view between those existing at the extreme positions of the adjustment, such as at any magnification between that of the image of C2 of maximum magnification and CA of minimum magnification. The lens elements of lens system D may be selected in accordance with any desired magnification or field of view that is required or desired.

The following discussion outlines an approach to the design of a suitable overall lens system for an ophthalmoscope in accordance with the invention, but this discussion is in no way intended to be limiting.

The simplest possible optical system would consist of a three-component afocal zoom system but this would need to produce an intermediate image of the retina in order to be able also to image the patient's pupil onto the clinician's pupil. For some zoom settings this intermediate image would be at the central zoom component and hence dirt etc may be visible in the final image. Furthermore, it would be preferable in some cases for the angular magnification range of the zoom system to be symmetrically disposed about unit angular magnification which often easier design of the zoom system.

Figure 2:
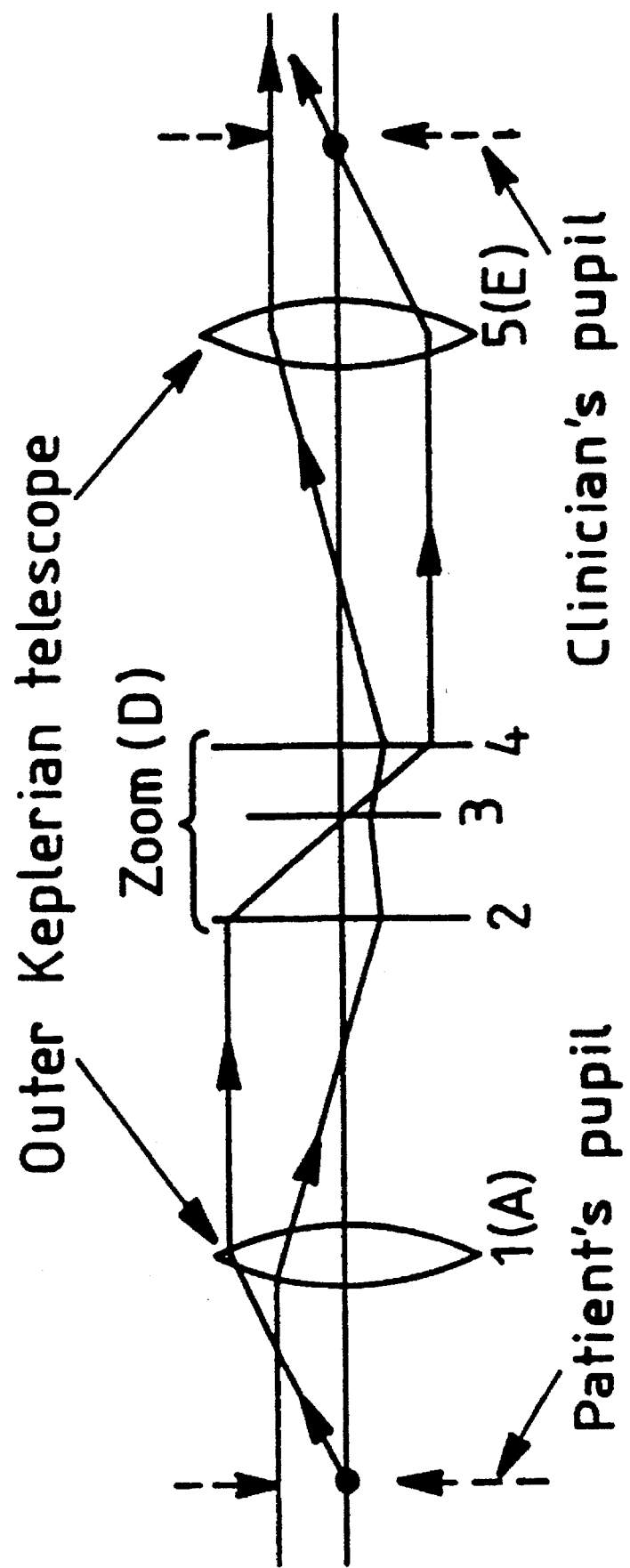
FIG. 2 is an optical diagram depicting in simple form the Gaussian design of the optical components of the instrument depicted in FIG. 1.
Figure 3:
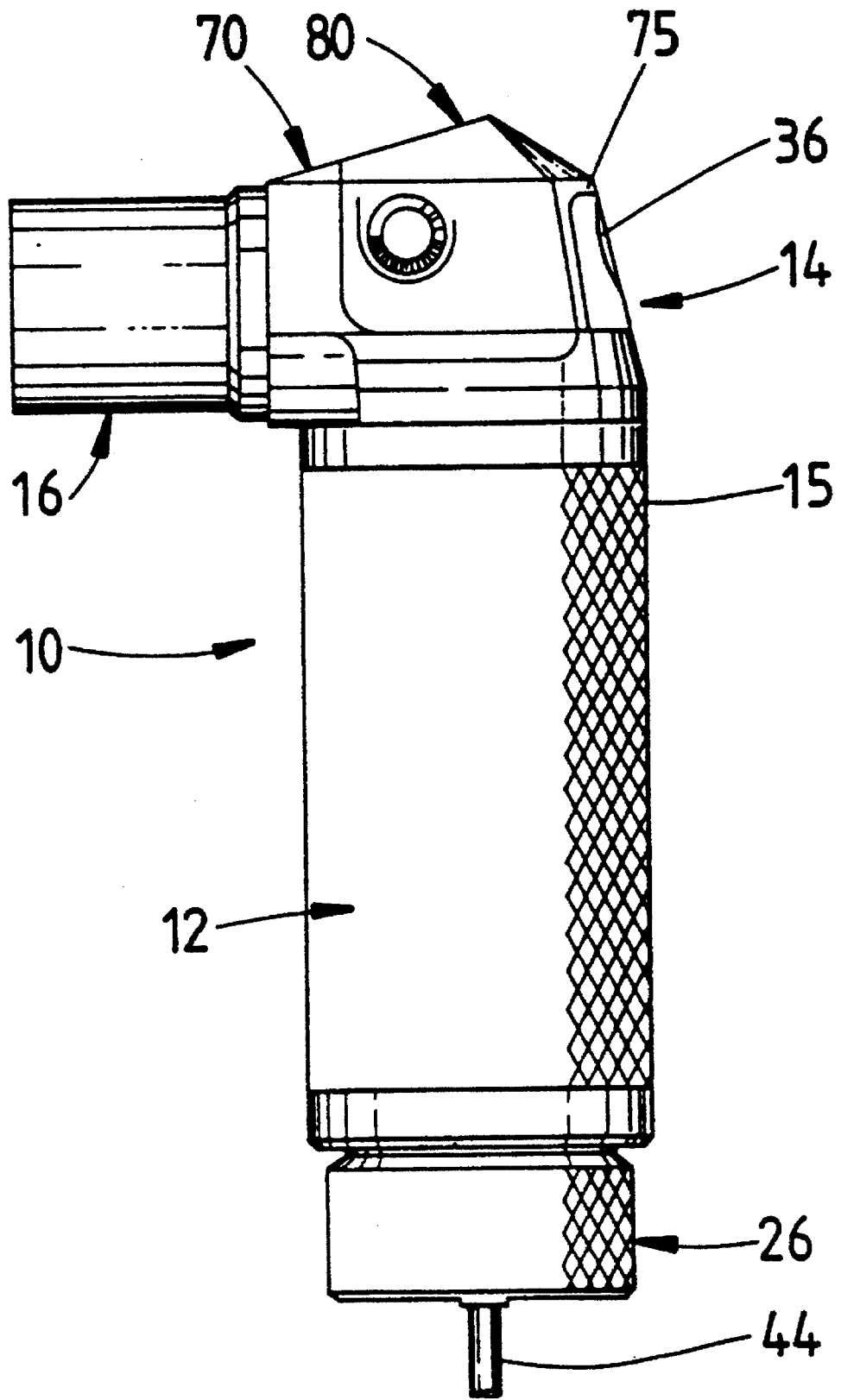
FIG. 3 is a side elevation of an instrument according to a second embodiment of the invention, incorporating both aspects of the invention in which the optical axis is folded to provide a compact hand-held instrument.
Figure 4:
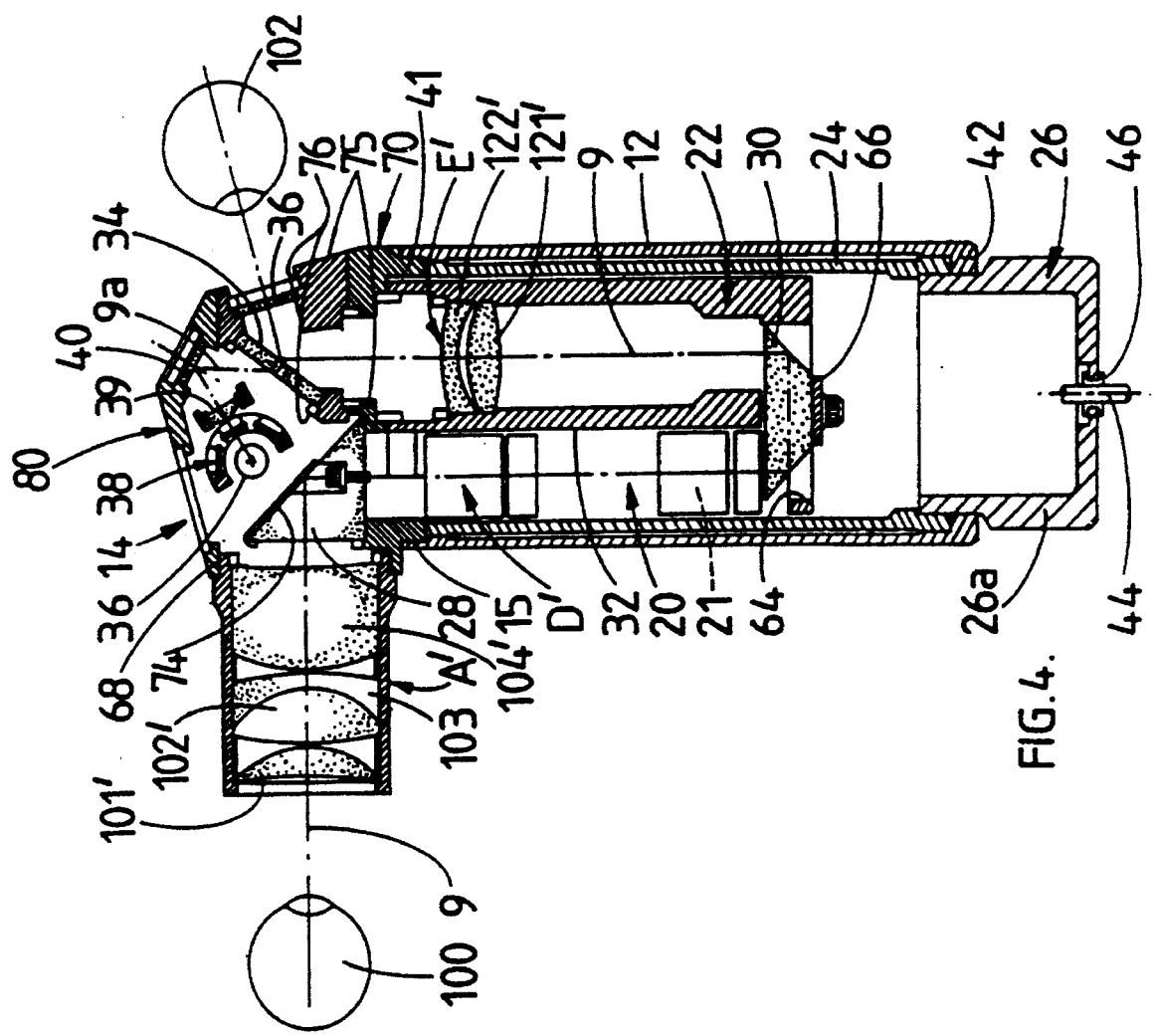
FIGS. 4 and 5 are respectively an axial cross-section and a partial cross-section of the instrument depicted in FIG. 3, the cross-sections being respectively on the axis of the objective lens assembly and normal to this axis (the orientations and views in FIG. 4 vary)
Figure 5:
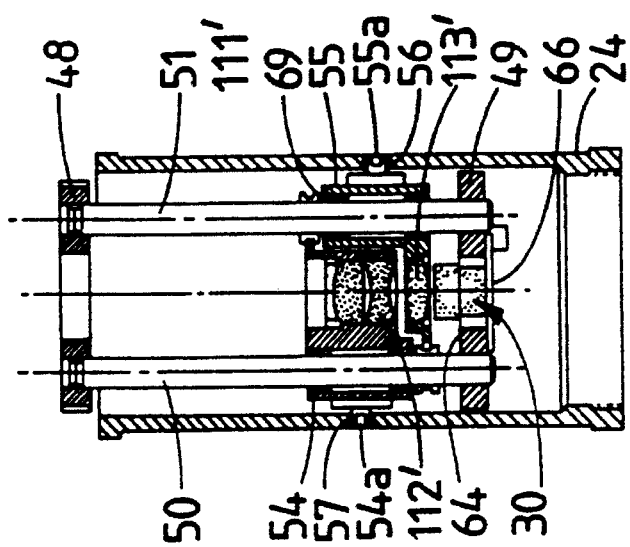

For the above reasons the overall system design shown in FIG. 2 was adopted. It can be seen to consist of an afocal zoom system working within a Keplerjan telescope.

The ophthalmoscope optical system of FIG. 1 preferably provides a magnifying power which ideally ranges from X15 to X3.75 and preferably embraces a zoom range up to X4 to X5, whilst having respective field sizes at least equal to those of the direct and indirect ophthalmoscopes at these two magnifications. The magnifying power MP of the optical system may be expressed as:

$$MP = \frac{\text{Angular size, at the eye, of the image}}{\text{Angular size, at the eye, of the object at Near Point}}$$

$$= u'/(F_E u/250)$$

$$= \frac{250 u'}{F_E u}$$

where u and u' are the paraxial pupil ray angles at the patient's and observer's pupils, respectively, and $F_E$ is the focal length of the patient's eye.

This may be written as:

$$MP = \frac{250}{F_E} M_A$$

where $M_A$ is the angular magnification of the whole optical system, and may itself be expressed as $$M_A = -\frac{F_1}{F_5} \times (M_T)_{zoom}$$

where $(M_T)_{zoom}$ is the transverse magnification of the zoom system and $F_1$ and $F_5$ are the focal lengths of lenses 1 and 5 in FIG. 2.

Substitution now gives:

$$MP = \left(\frac{250}{F_E}\right)\left(-\frac{F_1}{F_5}\right)(M_T)_{zoom}$$

$$= \left(\frac{250}{F_E}\right)\left(-\frac{F_1}{F_5}\right)\frac{1}{(M_A)_{zoom}}$$

where $(M_A)_{zoom}$ is the angular magnification of the zoom system. It is desirable that the zoom system has a symmetrically-disposed zoom range of angular magnification of 0.5:2.0, thus giving the preferred 4:1 range. Furthermore, at the maximum magnifying power MP=$(250/F_E)$ of the whole system, the zoom will have an angular magnification of $-0.5$ and therefore it is preferred that $(F_1/F_5)=0.5$.

A three-component, afocal system may be considered as a Keplerian telescope whose "objective" consists of the first two zoom components and whose "eyelens" is the third zoom component. Therefore the angular magnification of the zoom system may be written as:

$$M_A = -\frac{K_4}{K_{2,3}}$$

where $K_{2,3}$ is the combined power of the first two zoom components and may be represented as:

$$K_{2,3} = K_2 + K_3 - d_{23} K_2 K_3$$

Assuming that $K_3 = \lambda K_2$, substitution gives $$K_{2,3} = K_2 + \lambda K_2 - d_{23} \lambda K_2^2$$

$$\frac{1}{M_A} = -\frac{K_{2,3}}{K_4} = \frac{K_2}{K_4}(-1 - \lambda + d_{23} K_2) \quad (1)$$

From which $d_{23}$ can be determined. A similar formulation can be derived for $d_{34}$.

Such equations can be used to calculate the movements of the afocal zoom system by assuming values for $M_A, \lambda$ and the parameters of the lenses. The zoom system will be afocal for all zoom settings and so the image of the patient's pupil will remain in the same fixed position during zooming. As mentioned, the zoom system is a two-conjugate zoom system so that the image positions of both the patient's retina and the patient's pupil do not move during zooming. It is known to derive formulae covering the case where both conjugate pairs are at finite distances, but these do not apply to the present afocal zoom system, which is required to have one pair of infinite conjugates. Therefore it is necessary to use a different method of calculation. As discussed above, the values of $d_{23}$ and $d_{34}$ can be derived to indicate the relative positions of the three components of the zoom system which ensure that it is afocal for all zoom settings. The remaining requirement is that the throw of the zoom system, for the retinal imagery, should be the same for all zoom settings. (The throw is the distance from the object to the image.) The throw of a lens may be varied by moving it in relation to the object, which in this case is the retinal image formed by the first component of the ophthalmoscope. Therefore, it is desirable to calculate the position of the zoom lens, in relation to this retinal image, which will give the desired fixed throw for every zoom setting.

Unfortunately the customary conjugate formula $(1/\zeta - 1/l = K)$ cannot be used because the object and image distances, $l\zeta$ refer to the principal planes, which do not exist for an afocal system. However, if the position of a pair of conjugate planes $O_o, O_o'$) is known together with the transverse magnification, $M_o$, between them, then the position of other pairs of conjugate planes (such as O,O') may be calculated in the following way.

The paraxial marginal ray angles at $O_o$ and $O_o'$ are u and u' respectively which may be represented $$u = -\frac{\eta}{L'}, \; u' = -\frac{\eta'}{L'}$$

Therefore $$L = -\frac{\eta}{u'}, \; L' = -\frac{\eta'}{u'}$$

and $$\frac{L'}{L} = \frac{\eta' u}{\eta u'} = MM_o$$

where M is the transverse magnification between the planes at O,O' .

For an afocal system the transverse magnification is the same for all pairs of conjugate planes and therefore we have: where L'–L is the change in throw between the new conjugate O,O' pair and the known conjugate pair $O_o, O_o'$.

$$\text{Therefore, } L = \frac{\text{change in throw}}{(M_o^2 - 1)} \quad (2)$$

This formula may be used to calculate the necessary change in the object distance for the retinal imagery of the zoom system, in order to obtain the desired fixed throw. However, firstly we must calculate the position of the reference pair of conjugate planes at $O_o, O_o'$. It is convenient to adopt the plane containing the first zoom components as the object plane.

Using the customary conjugate formula $(1/\zeta - 1/l = K)$, consecutively for the last two components for the zoom system it is easily shown that:

$$l_4' = \frac{d_{23} - d_{34}(d_{23} K_3 - 1)}{d_{23} K_3 - 1 + K_4 [d_{23} - d_{34}(d_{23} K_3 - 1)]}$$

$$\therefore \text{Throw} = d_{23} + d_{34} + l_3' \quad (3)$$

for an object at the first component of the zoom system.

The required overall fixed throw for the retinal imagery of the zoom system may be calculated most easily for the $-1$ transverse magnification setting, for which the zoom system will be symmetrically-disposed with $d_{23}=d_{34}$. It is preferable to adopt λ=–2, as this will correct the Petzval curvature of the zoom system whilst leaving that of the overall system under-corrected since there will probably be some negative higher order field curvature and astigmatism.

Using the earlier formulas, values for $d_{23}$ and $d_{34}$ can be determined, and the overall throw calculated. It is this value of the throw for the retinal imagery which must be conserved for every zoom setting by calculating an appropriate value of L, the object distance fro the first zoom component in relation to the retinal image formed by the rust component of the overall system. For any zoom setting, L may be calculated from (2) and the value of $d_{12}$ is given by $F_1$–L.

The value of $d_{45}$ may then be calculated as follows:

$$d_{45} = \text{Throw} - L - d_{23} - d_{34} + F_5 \quad (4)$$

The lens movements for a zoom lens system may therefore be determined by adopting the following steps:

(a) Calculate the relative positions of the zoom components using (1) and corresponding formulas. This gives $d_{23}$ and $d_{34}$.

(b) Use (3) to calculate the throw of the zoom system, for an object at its rust component for each particular zoom setting.

(c) Obtain the value of L, the object distance in relation to the first zoom component (the object is the retinal image formed by the rust component of the overall system). This is calculated using (2). The value of $d_{12}$ is then given by $F_1$–L.

(d) Calculate $d_{45}$ from (4).

Since the relationships above interrelate focal length and power with spatial parameters, the design of a zoom lens system may be optimised to suit known physical constraints or preferments.

Table 1 sets out the parameters of a practical lens configuration according to an embodiment of the invention. The configuration is depicted in FIG. 1 and consists of three lens units—a 4-lens unit 100 for lens system A2, a triplet 110 for zoom lens system D, and a doublet 129 for eyepiece system E.

TABLE 1

| Lens FIG. 1 | Type | Radius of Front Face | Radius of Back Face |
|---|---|---|---|
| 101 | Concave-convex | –129.8 mm | –21.81 mm |
| 102 | Biconvex | 60.56 mm | –18.68 mm |
| 103 | Concave-convex | –18.68 mm | –83.13 mm |
| 104 | Convex-concave | 38.10 mm | 255.3 mm |
| 111 | Biconvex | 13.38 mm | –31.22 mm |
| 112 | Biconcave | –15.51 mm | 9.20 mm |
| 113 | Biconvex | 28.54 mm | –11.22 mm |
| 121 | Biconvex | 46.27 mm | –23.11 mm |
| 122 | Concave-convex | –20.23 mm | –36.24 mm |

Lenses 102, 103 are in contact as a doublet.

An exemplary arrangement for the embodiment of FIG. 1 and Table 1 is for lens system A2 to be arranged to be locatable in use about 25 mm from the patient's pupil, with the distance between lens systems A2 and E being of the order of 340 mm and the distance between lens system E and the observer's pupil in use being about 65 min. In some embodiments, the combined or overall focal length of the zoom system may be of the order of about one quarter of the distance between the images located on either side of the zoom lens system.

Table 2 indicates results obtained for magnification and field of view in another such arrangement

TABLE 2

| Magnification (Angular) | Diameter of Field of View | |
|---|---|---|
| | Object | Image |
| × 15 | 14° | 14° |
| × 7.5 | 28° | 14° |
| × 3.75 | 53° | 14° |
| | (Patient's eye) | (Observer's eye) |

The purpose of Table 2 is to show how the fields of view (object and image) vary with magnification. This table describes one approach to the ophthalmoscope design in which the image field of view diameter is constant at 14°. The object field diameter then is related to this value and the magnification M by the equation:

tan (object field radius)/tan(image field radius)×magnification: 15

For example, take the 3.75 magnification values. Here tan(53/2)/tan(14/2)×3.75=15.2 which is approximately 15. It is clear that there the object field value of 53° is only approximate. A more accurate value is 52.3°.

Another approach to the design would be to keep the object field diameter constant and have the image field changing with magnification.

A third approach would be to allow both object and image fields to vary with magnification.

Finally, it should be noted that the object and image field diameters given in the above table for the x15 magnification are probably higher than usually achieved in direct ophthalmoscopy. These values would require the patient to clinician eye distance to be about 30 mm. A more usual distance is about 50–60 mm, which would reduce the magnification and/or field size accordingly.

FIGS. 3 to 8 depict a second embodiment d ophthalmoscope 10 according to both aspects of the invention, which has a folded axis configuration and is of compact hand-held form. This instrument 10 incorporates an optical system similar to that depicted in straight line configuration in FIG. 1, and like primed reference numerals are utilised to indicate corresponding optical components. Lens parameters are similar to those indicated in Table 1 as these lend themselves to a folded configuration of the kind depicted in FIGS. 3 to 8.

Instrument 10 includes an outer cylindrical casing 12 arranged for use with its axis vertical, a head assembly 14 threadingly engaged at 15 atop casing 12, a forwardly projecting objective lens assembly A' interchangeably fitted to head assembly 14, and an adjustable lens mechanism 20 including a zoom lens system D', an internal spool assembly 22, and co-operating sleeve 24 rotatable by a depending knob 26. In use, casing 12 is held in the hand and then serves as a handle for the instrument. The optical path is indicated at 9. Light from the patient's eye 100 passes through objective lens assembly A' and is diverted downwardly at the front of casing 12, by a triangular prism 28, through moveable zoom lens system D'. It is then reversed by a double prism 30 back up a rear tube 32 of spool assembly 22 through eyepiece lens system E' and thence via a transparent mirror :34 to the inclined eyepiece 35 for viewer 102 at the rear of head assembly 14. Illumination is provided by a small incandescent lamp 36 in head assembly 14 which eaten light path 9 along optical path 9a through mirror :34, via one of three selectable fitters 38, a collimating lens 39 and a mirror 40.

Sleeve 24 is rotatably retained within casing 12 between a depending shoulder 41 on head assembly 14 and an internal lip 42 at the lower end of the casing. Knob 26 is a hollow body with an upstanding tubular portion 26a fixed within sleeve 24. The knob projects through lip 42 and is externally knurled for enhanced grip. The electrical supply lead 44 for lamp 36 is lead through a bush 46 at the centre of knob 26.

Spool assembly 22 includes respective upper and lower plates 48, 49 to which tube 32 is welded. Upper plate 48 is fastened to head assembly 16 whereby the whole spool assembly is suspended within sleeve 24. The plates 48, 49 are also coupled by a pair of posts 50, 51 in front of tube 32. Slidably supported on these posts are the holders 54, 55 for respective lenses 111', 112', 113' of zoom lens system D'. Each holder 54, 55 carries a projection 54a, 55a which travels along respective part helical slots 56, 57 in sleeve 24, whereby rotation of the sleeve by means of knob 26 causes the lenses 111', 112', 113' to travel up and down between plates 48, 49. It is to be noted that the slots 56, 57 are not necessarily parallel: the lenses 111', 112', 113' are discussed further below.

Plate 48 includes a front recess 60 below prism 28 and an open top 32a for robe 32, while plate 49 has a slot 64 directly below prism 28 and an open bottom for tube 32. Double prism 30 is fixed on a mounting strap 66 bolted under plate 49 and lies in slot 64.

As before, zoom lens system D' is of two conjugate configuration, ie where two pairs of conjugate planes—object/image and entrance/exit pupils—are kept stationary as the focal length, field of view and magnification change. As best seen from FIG. 8, lens system 21 comprises, in the order encountered along optical path 9 travelling away from the patient's eye, a double convex lens 113' and a double concave lens 112' in holder 54, and a second double convex lens 111' in holder 55. Each lens is retained against a respective shoulder of a bore in its holder by a conventional snap-in ting, and the precise optical characteristics of the six interfaces are preselected, in conjunction with the relative movement of the holders determined by the form of slots 56, 57, to achieve the desired two-conjugate system. Each holder has bearing sleeves 69 for smooth travel along posts 50, 51.

Objective lens assembly A, incorporating lens 101'–104', substitutes for the hand-held interchangeable condensing lens typical of prior indirect ophthalmoscopes and is screwed into a complementary aperture 68 in head assembly 14.

Figure 6:
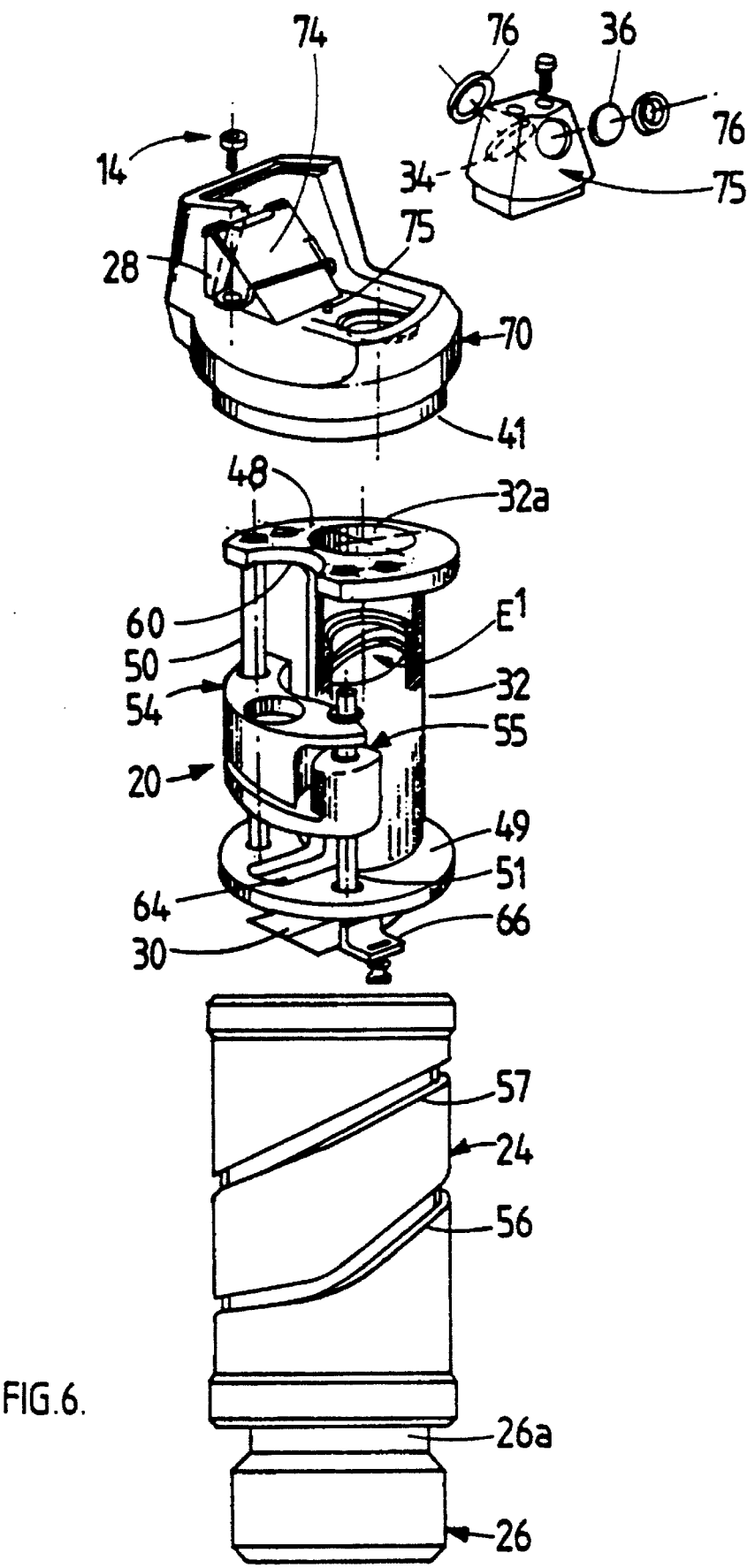
FIG. 6 is a partially exploded view showing various parts of the instrument of FIGS. 3 to 5.

Head assembly 14 is in three principal parts, best seen in FIGS. 6 and 7. A main body 70 carries objective lens aperture 68, depending threaded shoulder 41 for engaging casing 12, and an inverted saddle 74 for retaining prism 28 in place against a centre stop 75. Appropriate apertures are provided below prism 28 and above tube 32. A hollow cast or moulded insert 75 for head main body 70 locates above tube 32 and carries opening for mirror 34 and eyepiece 35, both retained by suitable rings 76. A shaped cover 80 for head assembly 14 (FIG. 7) has a rear opening 82 which fits about insert 75 and side skirts 84, 85 with apertures and seats which respectively mount a bracket 86 for lamp 36 and a mechanism 88 for selecting filters 38.

Bracket 86 is L-shaped so as to define a front arm 86a for lamp collimating lens 39, and a front aperture 89 in cover 80 houses lamp mirror 40 and an overlying closure cap 90.

Filter selection mechanism 88 has an externally rotatable knob 92, an internal half-sleeve 94 with seat apertures for the selectable filters 38, and an interconnecting shaft assembly 96. Assembly 96 includes an indexing device 97 with a springloaded ball (not visible) engageable with blind bores 98 in a boss of half-sleeve 94.

In an alternative construction, illumination might be more direct, eg through prism 28 rather than mirror :34. Moreover, the arrangement may alternatively be such that the observer's line of sight is at least collinear and preferably co-axial with the patient's eye line. The illustrated instrument is monocular but a binocular modification may of course be provided. The zooms lens system D' may of course be driven by a motor and thread or worm arrangement, or by any other powered device, instead of the hand-operated configuration illustrated.

The main advantage of the illustrated instrument is the need to use only one type of ophthalmoscope in contrast to the traditional requirement for two separate instruments—an indirect one to first locate the area of abnormality and to obtain an overall view of the condition of the eye in order that a study of the fundus features may be undertaken, and then a direct instrument in order to study significant portions of the fundus features in more detail at a higher magnification. When examining the fundus, ideally one looks with an indirect instrument and then, having obtained an overview, swaps to a direct ophthalmoscope to examine the feature of interest in detail. The improved ophthalmoscope of the present invention allows for a continuously variable range of magnification and field of view so that the appropriate magnification and field of view can be selected to view any sized feature of the fundus at any magnification that is desired without the need to realign or refocus as is required when alternately using the two types d instruments.

These advantages are achieved in an instrument with a zoom range up to X4 to X5, with a zoom lens system of two-conjugate configuration, and with a highly practical compactness which successfully folds the optical path into a practical form while accommodating the three lens systems and the necessary movements of the zoom lens system.

The continuously variable magnification allows an observer to zoom in on an object of interest without interrupting the viewing of the features or without losing the feature. This can be a problem when one instrument is replaced by another to permit the object of interest to be viewed at different magnifications.

Some features or conditions are more easily visible with an indirect ophthalmoscope while other features are only visible with a direct ophthalmoscope. The apparatus of the present invention provides sufficient versatility to cover all conditions with a single instrument only.

In a modification, an annular surround field of view may provide a 'direct' view of the eye, i.e. the front of the eye or the iris plane as the operator or clinician would view the eye unaided. Thus, there would be two views of the patient's eye using the annular surround, a core view which could be magnified to any extent, and a peripheral or annular view of the patient's eye as it appears to the naked eye of the observer. The purpose or advantage of this modification is to aid in the location and alignment of the instrument, particularly during movement across the eye as one 'scans' the eye searching for the presence of abnormalities.

We claim:

1. An optical instrument for indirectly observing an object, comprising a first lens system for producing a first image of the object, and an adjustable second lens system for producing a second image of the object, said second lens system being continuously adjustable between a first position wherein the second image has maximum magnification and/or a minimum area of view and a second position wherein the second image is of a minimum magnification and/or a maximum area of view, wherein said second lens system is a zoom lens system having two substantially fixed conjugates.

2. An optical instrument according to claim 1, wherein said zoom lens system is an afocal lens system having one pair of substantially infinite conjugate planes.

3. An optical instrument according to claim 1, wherein said zoom lens system comprises three mutually movable lenses.

4. An optical instrument according to claim 3, wherein said first lens system comprises a unit of four distinct lenses, and said instrument includes a third lens system serving as an eyepiece lens system.

5. An optical instrument according to claim 1, wherein the instrument comprises an ophthalmoscope dimensioned for the eye of the observer to observe an eye of a patient, wherein the two fixed conjugates of the zoom lens system comprise the image positions of the patient's retina and pupil.

6. An optical instrument for indirectly observing an object, comprising a first lens system for producing a first image of the object, and an adjustable second lens system for producing a second image of the object, said second lens system being continuously adjustable between a first position wherein the second image has maximum magnification and/or a minimum area of view and a second position wherein the second image is of a minimum magnification and/or a maximum area of view, wherein said optical instrument defines a folded optical path which includes a generally U-shaped portion so as, in use, to reduce the separation of the observer and the observed object.

7. An optical instrument according to claim 6, wherein said adjustable second lens system is in an arm of said generally U-shaped portion, said first lens system is in a further portion of said optical path which projects substantially normally relative to said arm, and there is further provided an eyepiece lens system for observing said second image of the object.

8. An optical instrument according to claim 7, wherein said generally U-shaped portion of said optical path is provided with a casing adapted to be held in an observer's hand.

9. An optical instrument according to claim 8 including means for sliding said second lens system along said arm of the generally U-shaped optical path portion.

10. An optical instrument according to claim 9, wherein said sliding means comprises a sleeve and means to rotate the sleeve, and said second lens system is retained in a plurality of holders which are slidably disposed on a pair of posts and which have projections in engagement with guideways in said sleeve.

11. An optical instrument according to claim 6, further including a plurality of prisms defining the respective folds in said optical path.

12. An optical instrument according to claim 6, wherein said second lens system is a zoom lens system.

13. An optical instrument according to claim 12, wherein said zoom lens system has two substantially fixed conjugates.

14. An optical instrument according to claim 13, wherein said zoom lens system is an afocal lens system having one pair of substantially infinite conjugate planes.

15. An optical instrument according to claim 13, wherein said zoom lens system comprises three mutually movable lenses.

16. An optical instrument according to claim 15, wherein said first lens system comprises a unit of four distinct lenses, and said instrument includes a third lens system serving as an eyepiece lens system.

17. An optical instrument according to claim 6, wherein the instrument comprises an ophthalmoscope dimensioned for the eye of the observer to observe an eye of a patient.

18. A method, comprising the steps of:

indirectly observing an eye of a patient with the eye of an observer through an ophthalmoscope;

producing a first image of the eye through a first lens system in said ophthalmoscope; and producing a second image of the eye through an adjustable second lens system in said ophthalmoscope, said second lens system being continuously adjustable between a first position wherein the second image has maximum magnification and/or a minimum area of view and a second position wherein the second image is of a minimum magnification and/or a maximum area of view, wherein said second lens system is a zoom lens system having two substantially fixed conjugates.

19. The method of claim 18, wherein said step of observing comprises viewing the patient's retina and pupil wherein the two fixed conjugates of the zoom lens system comprise the image positions of the patient's retina and pupil.

20. A method, comprising the steps of:

indirectly observing an eye of a patient with the eye of an observer through an ophthalmoscope;

producing a first image of the eye through a first lens system in said ophthalmoscope; and producing a second image of the eye through an adjustable second lens system in said ophthalmoscope, said second lens system being continuously adjustable between a first position wherein the second image has maximum magnification and/or a minimum area of view and a second position wherein the second image is of a minimum magnification and/or a maximum area of view, wherein said ophthalmoscope defines a folded optical path which includes a generally U-shaped portion so as, in use, to reduce the separation of the observer and the observed object.

21. The method of claim 20, wherein said step of observing comprises viewing the patient's retina and pupil, wherein said second lens system is a zoom lens system having two substantially fixed conjugates and wherein the two fixed conjugates of the zoom lens system comprise the image positions of the patient's retina and pupil.

* * * * *